United States Patent [19]
Andrews et al.

[11] Patent Number: 5,625,064
[45] Date of Patent: Apr. 29, 1997

[54] PROCESS FOR THE PREPARATION OF TRIAZOLONES

[75] Inventors: David R. Andrews, Maplewood; Dinesh Gala, East Brunswick, both of N.J.; Jacques Gosteli, Basel; Frank Guenter, Langnau, both of Switzerland; William Leong, Westfield, N.J.; Ingrid Mergelsberg, Dagmersellen, Switzerland; Anantha Sudhakar, East Brunswick, N.J.

[73] Assignee: Schering Corporation, Kenilworth, N.J.

[21] Appl. No.: 458,550

[22] Filed: Jun. 2, 1995

Related U.S. Application Data

[63] Continuation of Ser. No. 425,028, Apr. 19, 1995.

[51] Int. Cl.$^6$ ................................................ C07D 403/10
[52] U.S. Cl. .................... 544/366; 548/264.6; 548/263.2
[58] Field of Search ................. 544/366; 548/263.2, 548/264.6

[56] References Cited

U.S. PATENT DOCUMENTS

| | | | |
|---|---|---|---|
| 4,028,344 | 6/1977 | Lange et al. | 260/174 |
| 4,619,931 | 10/1986 | Heeres et al. | 514/252 |
| 4,735,942 | 4/1988 | Heeres et al. | 514/252 |
| 4,791,111 | 12/1988 | Heeres et al. | 514/252 |
| 4,861,879 | 8/1989 | Heeres et al. | 544/55 |
| 5,039,676 | 8/1991 | Saksena et al. | 514/254 |
| 5,256,793 | 10/1993 | Bailey et al. | 548/263.2 |
| 5,403,937 | 4/1995 | Saksena et al. | 548/268.8 |

FOREIGN PATENT DOCUMENTS

| | | |
|---|---|---|
| 0283992 | 9/1988 | European Pat. Off. . |
| WO89/04829 | 6/1989 | WIPO . |
| WO93/09114 | 5/1993 | WIPO . |
| WO94/11357 | 5/1994 | WIPO . |
| WO94/25452 | 11/1994 | WIPO . |

OTHER PUBLICATIONS

Greene, et al., "Protective Groups in Organic Synthesis", 2 ed., pp. 10–142, John Wiley & Sons (New York, 1991).

Kobayashi, et al., Bull. Chem. Soc. Jpn., 62, 3038–3040 (1989).

Temple, Jr., et al., "Triazoles 1,2,4", The Chemistry of Heterocyclic Compounds, John Wiley & Sons, New York (1981), pp. 372–373.

Temple et al, "Triazoles 1,2,4" The Chemistry of Heterocyclic Compounds John Wiley & Sons, N.Y. (1981) pp. 457–459.

Cram & Hammond, "Organic Chemistry", 2nd Edition, McGraw Hill Book On, N.Y. (1964) pp. 565–567 & pp. 249–251 & pp. 377–379 & pp. 250–251 & pp. 351–352.

Primary Examiner—John M. Ford
Attorney, Agent, or Firm—John Blasdale

[57] ABSTRACT

Described is a process for preparing triazolone compounds of the formula

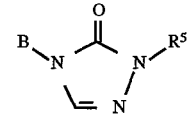

comprising heating a mixture of a compound of the formula

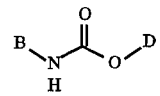

and a hydrazine derivative of the formula $R^5$—NH—NH—CHO, $R^5$—NH—NH—C(O)OC(CH$_3$)$_3$ or $R^5$—NH—NH—C(O)OCH$_2$C$_6$H$_5$, optionally in the presence of an added base.

19 Claims, No Drawings

PROCESS FOR THE PREPARATION OF TRIAZOLONES

The present application is a continuation of U.S. application Ser. No. 08/425,028 filed Apr. 19, 1995.

The present invention comprises a process for preparing triazolones and more particularly for preparing trisubstituted tetrahydrofuran triazole antifungals.

BACKGROUND OF THE INVENTION

PCT International Publication Nos. WO 89/04829 and WO 93/09114, and U.S. Pat. No. 5,039,676 disclose substituted tetrahydrofuran azole and imidazole compounds having utility as antifungal agents. Dioxolanyl imidazole and triazole antifungal agents and related compounds are described in U.S. Pat. Nos. 4,619,931, 4,861,879, 4,735,942 and 4,791,111. A number of processes for the synthesis of these compounds are known.

For example, PCT International Publication No. WO93/09114 discloses a process for the synthesis of trisubstituted tetrahydrofuran azole antifungals by reacting a tosylate of the formula (I)

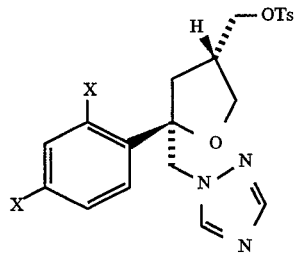

wherein X is both F or both Cl or one X is F and the other is Cl, with a compound of the formula (II)

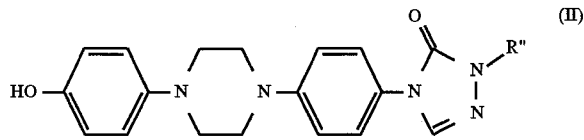

wherein R" is alkyl, alkenyl, alkynyl cycloalkyl, etc. The synthesis of a compound of the formula (I) is described in PCT International Publication No. WO94/25452. WO93/09114 also describes the conversion of a compound of the formula

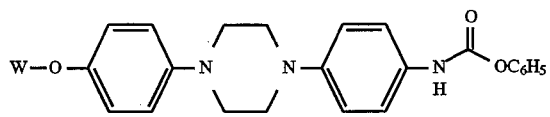

wherein W represents

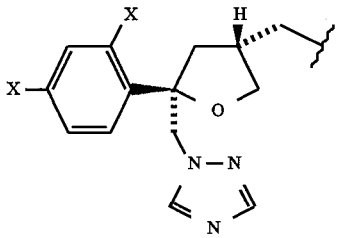

to a compound of the formula

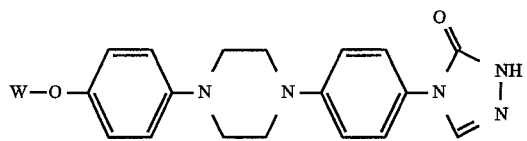

which is subsequently N-alkylated to give a compound of the formula

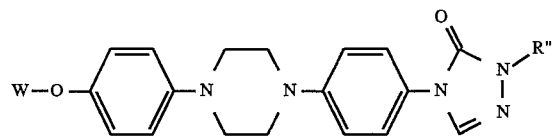

wherein R" is as defined above.

N-alkylation of the triazolone group as described in the prior art is inefficient, requiring a large excess of an expensive alkylating agent, typically an alkyl bromide, and results in a mixture of N-alkylated and O-alkylated triazolone products, necessitating laborious purification methods and giving low yields of the N-alkylated triazolone.

SUMMARY OF THE INVENTION

The present invention solves the aforementioned problems by providing an efficient process for preparing N-substituted triazolones. In a preferred embodiment, the instant process provides a method for preparing N-alkylated triazolone intermediates which are useful in the synthesis of tetrahydrofuran azole antifungal agents. The instantly claimed process is free of competing O-alkylation reactions, avoids the need for a large excess of alkylating agent, and proceeds in good yield producing a product of high purity. The process of the present invention utilizes inexpensive starting materials and can be used to prepare a wide variety of N-alkyl triazolone intermediates.

The process of the present invention comprises heating a mixture of a compound of the formula

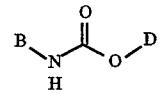

wherein:

B is aryl, substituted aryl or a group of the formula

wherein

R is $C_6H_5CH_2$, $CH_3$, H or a group of the formula

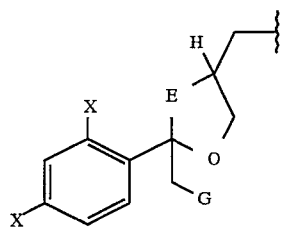

where

G is imidazolyl or triazolyl, E is $CH_2$ or O, and each X is independently F or Cl; and D is $C_1$–$C_6$ alkyl, aryl, substituted aryl or aryl($C_1$–$C_6$ alkyl); with:

(a) a hydrazine derivative of the formula Z—NH—NH—$R^5$, wherein $R^5$ is $C_1$–$C_{20}$ alkyl or substituted $C_1$–$C_{20}$ alkyl, and Z is —CHO; or (b) a hydrazine derivative of the formula Z—NH—NH—$R^5$, wherein $R^5$ is as defined above and Z is —C(O)OC($CH_3$)$_3$ or —C(O)OCH$_2$C$_6$H$_5$, followed by hydrolyzing the Z group, and heating with a trialkylorthoformate and formic acid, to form a triazolone of the formula

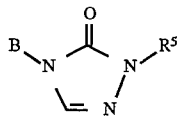

wherein B and $R^5$ are as defined above. The process of the present invention is optionally carried out in the presence of an added base.

In a preferred embodiment, the present invention provides a process for preparing compounds of the formula (III)

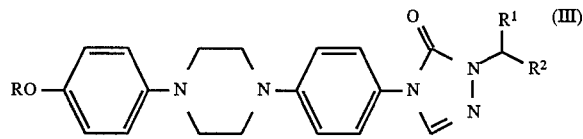

wherein:

R is $C_6H_5CH_2$, $CH_3$, H or W;

$R^1$ and $R^2$ are independently $C_1$–$C_6$ alkyl or Y-substituted $C_1$–$C_6$ alkyl, wherein Y is —OH or —$OR^4$, and wherein $R^4$ is a hydroxyl protecting group;

or $R^1$ and $R^2$ together with the carbon atom to which they are attached comprise a $C_4$–$C_7$ carbocyclic ring or a Y-substituted $C_4$–$C_7$ carbocyclic ring, wherein Y is as defined above; and W represents

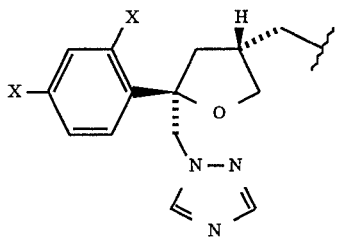

wherein each X is independently Cl or F;

comprising heating a compound of the formula (IV)

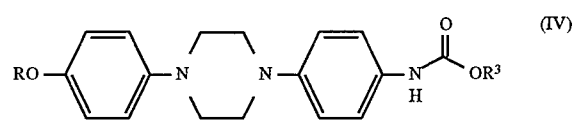

wherein R is $C_6H_5CH_2$, H, $CH_3$ or W, and $R^3$ is phenyl, with:

(a) a hydrazine derivative of the formula $R^1R^2$CH—NH—NH—Z, wherein Z is —CHO, and $R^1$ and $R^2$ are as defined above, provided that Y is —$OR^4$; or (b) a hydrazine derivative of the formula $R^1R^2$CH—NH—NH—Z, wherein Z is —C(O)OC($CH_3$)$_3$ or —C(O)OCH$_2$C$_6$H$_5$, and $R^1$ and $R^2$ are as defined above, provided that Y is —$OR^4$, followed by hydrolyzing the Z group, and heating with a trialkylorthoformate and formic acid, to form a compound of the formula (III)

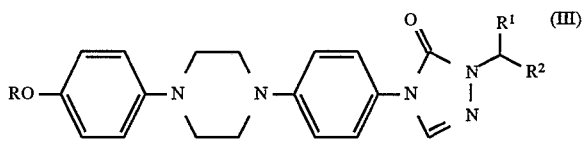

wherein R, $R^1$ and $R^2$ are as defined above provided that Y is —$OR^4$. Compounds of the formula (III) wherein Y is —OH are prepared by deprotecting a compound of the formula (III) wherein Y is —$OR^4$. Treating a compound of the formula (III), wherein R is $C_6H_5CH_2$ or $CH_3$, with HBr provides a compound of the formula (IIIa)

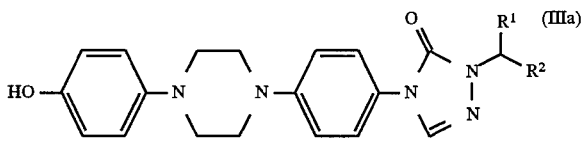

wherein $R^1$ and $R^2$ are as defined above, i.e., a compound of the formula (III) wherein R is H.

The present invention further comprises a process for converting a compound (III), as defined above, having the structural formula (XVII)

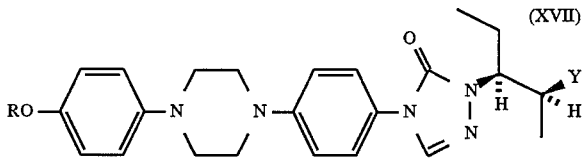

wherein R is H and Y is —$OR^4$, to a compound of the formula (XVII) wherein R is W, comprising reacting a compound of the formula (XVII), wherein R is H, with a compound of the formula

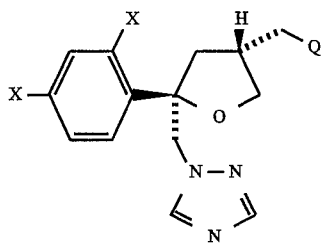

wherein Q is a leaving group and X is as defined above, in the presence of a base, and optionally deprotecting to form a compound (XVII) wherein R is W and Y is —OH.

In a more preferred embodiment the present invention provides a process for preparing compounds of the formula (III) as described above wherein the hydrazine of formula $R^1R^2CH$—NH—NH—Z is prepared via a process comprising the steps:

(a) reacting a ketone of the formula $R^1R^2C(O)$, wherein $R^1$ and $R^2$ are as defined above provided that Y is —$OR^4$, with a compound of the formula $H_2N$—NH—Z, wherein Z is as defined above, to form a compound of the formula $R^1R^2C$=N—NH—Z; and (b) reducing the product of step (a) to form a compound of the formula $R^1R^2CH$—NH—NH—Z.

DETAILED DESCRIPTION

All publications cited herein are incorporated in their entirety by reference.

As used herein, the term:

"alkyl" means a straight or branched alkyl chain having the number of carbon atoms specified; and "substituted alkyl" means an alkyl group bearing one to three substituents selected from halo, $C_1$-$C_6$ alkoxy, aryloxy;

"aryl" means a carbocyclic aromatic group, such as phenyl or naphthyl; and "substituted aryl" means an aryl group bearing one to three substituents selected from halo, alkyl, $C_1$-$C_6$ alkoxy;

"halo" means a fluoro, chloro, bromo or iodo group;

"aryl(alkyl)" means an alkyl group substituted by an aryl group, benzyl for example;

"hydride reducing agent" means a metal hydride reagent, such as $NaBH_4$, Red-Al, DIBAL-H, L-Selectride, Vitride, $LiBH_4$, $LiAlH_4$, $LiAl(OtBu)_3H$, $NaCNBH_3$, DMAB, zinc borohydride, calcium borohydride, a combination of $LiBH_4$ and $ZnBr_2$, or a combination of $NaBH_4$ and LiCl;

"base" means a non-nucleophilic basic compound capable of facilitating the reaction between a compound of the formula (IV) and a hydrazine of the formula $R^1R^2CH$—NH—NH—Z, such as a tertiary amine base, hydroxide base, DBU, DBN, Dabco, a moderate base or phosphazene base;

"moderate base" means $Na_2CO_3$, $Li_2CO_3$ or $K_2CO_3$;

"phosphazene base" means a base which is a cyclic or linear oligomer or polymer comprising alternating nitrogen and phosphorous atoms, such as a cyclic trimer or cyclic tetramer, having two substituents on each phosphorous atom;

"tertiary amine base" means bases such as $Et_3N$, DMAP or Hünigs base, as well as analogous polymer supported bases comprising one or more tertiary amino groups;

"hydroxide base" means an alkali metal hydroxide, such as NaOH, KOH or LiOH, or $Bu_4NOH$; and "trialkylorthoformate" means an orthoester of the formula HC(O-alkyl)$_3$, wherein each O-alkyl group comprises from 1–6 carbon atoms, such as O—$CH_3$, O$C_2H_5$O—$C_3H_7$ and O—$C_4H_9$.

As used herein the following reagents and solvents are identified by the abbreviations indicated: methanol (MeOH); t-butyl methyl ether (TBME); triethylamine ($Et_3N$); sodium bis(2-methoxyethoxy)aluminum hydride (Red-Al); di-isobutylaluminum hydride (DIBAL-H); lithium tri(sec-butyl)borohydride (L-Selectride); Vitride; lithium tri-t-butoxyaluminohydride ($LiAl(OtBu)_3H$); t-butylamineborane (tBu$NH_2$·$BH_3$); dimethylamineborane (DMAB); di-isopropylethylamine (Hünigs base); 1,2-dimethoxyethane (DME); 1,8-diazabicyclo[5.4.0]undec-7-ene (DBU); ethanol (EtOH); 14-diazabicyclo[2.2.2]octane (Dabco); tetrabutylammonium hydroxide ($Bu_4NOH$); 1,5-diazabicyclo[4.3.0]non-5-ene (DBN); pyridinium p-toluenesulfonate (PPTS); acetic acid (HOAc); N-t-butoxycarbonylhydrazine (BOC-hydrazine); dibenzoyl-D-tartaric acid (D-DBTA); dibenzoyl-L-tartaric acid (L-DBTA).

The "hydroxyl protecting group", $R^4$, is a protecting group which blocks an —OH group thereby preventing reactions involving the —OH group from occurring during the process of the present invention. Hydroxyl protecting groups are well known in the art and methods for the formation and removal of hydroxyl protecting groups are also well known such as those described in Greene, et al., "Protective Groups in Organic Synthesis", 2nd ed., John Wiley & Sons, 10–142 (New York 1991). Preferred hydroxyl protecting groups for use in the present invention are ethers, such as benzyl ether.

The term "leaving group" means a substituent which is susceptible to displacement by a suitable nucleophile, and includes groups such as halo; $C_1$-$C_6$ alkoxy; —$OS(O)_2R^5$ wherein $R^5$ is $C_1$-$C_4$ alkyl, $CF_3$, aryl, substituted aryl or aryl($C_1$-$C_4$ alkyl); or —$OC(O)R^6$ wherein $R^6$ is $C_1$-$C_6$ alkyl, $C_1$-$C_6$ alkoxy, aryl or substituted aryl. The particular leaving group to be used is in part dependent upon the strength of the nucleophile, with more labile groups, such as halo and in particular —$OS(O)_2R^5$, being used in conjunction with weaker nucleophiles. The leaving group Q is preferably a group of the formula —$OS(O)_2R^5$, wherein $R^5$ is as defined above, and is more preferably such a group wherein $R^5$ is selected from —$CH_3$, —$CF_3$, —$C_6H_5$, —$C_6H_4CH_3$, —$C_6H_4Br$ and —$C_6H_4Cl$. The leaving group L is preferably: $C_1$-$C_6$ alkoxy, halo or —$OC(O)R^6$, wherein $R^6$ is as defined above.

The present invention comprises a process for preparing a triazolone of the formula (X) as shown in Reaction Scheme 1.

Reaction Scheme 1

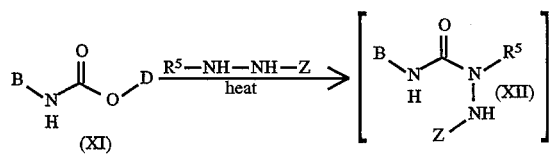

-continued
Reaction Scheme 1

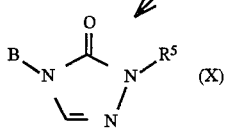

In Reaction Scheme 1, compound (XI) is heated at 50° to 90° C. with a hydrazine of the formula $R^5$—NH—NH—Z, wherein B, D, $R^5$ and Z are as defined above, optionally in the presence of a base, such as $Et_3N$, DBU, $K_2CO_3$ or a phosphazene base, in a suitable solvent, such as toluene, to form an intermediate of the formula (XII). Upon further heating at 80° to 150° C., the intermediate (XII) is converted to a compound of the formula (X).

In a preferred embodiment the present invention comprises a process for preparing a compound of the formula (III) as shown in Reaction Scheme 2.

Reaction Scheme 2

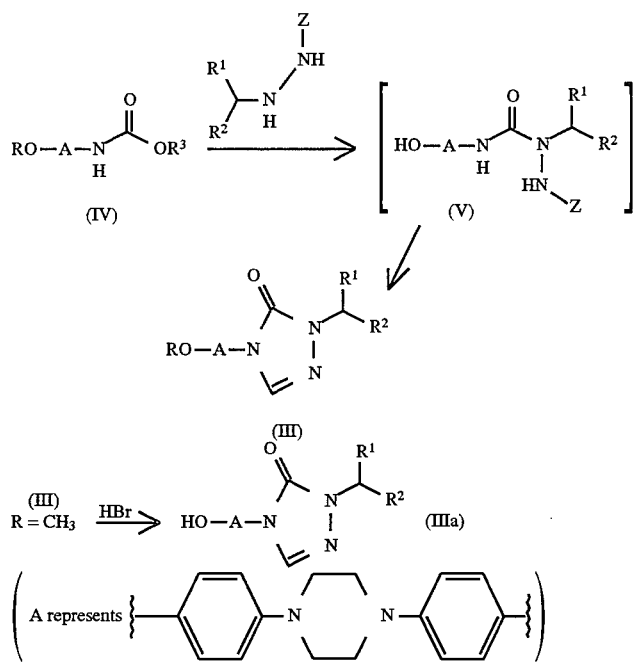

In Reaction Scheme 2, compound (IV), wherein R and $R^3$ are as defined above, is heated at 50° to 90° C. with a hydrazine of the formula $R^1R^2CH$—NH—NH—Z, wherein $R^1$, $R^2$ and Z are as defined above, provided that Y is —$OR^4$, in the presence of a base, such as $Et_3N$, DBU, $K_2CO_3$ or a phosphazene base, in a suitable solvent, such as toluene, to form an intermediate of the formula (V). The intermediate (V) is not isolated and upon further heating at 80° to 150° C., the intermediate (V) is converted to a compound of the formula (III) wherein R, $R^1$ and $R^2$ are as defined above, provided that Y is —$OR^4$.

The compound (III), wherein Y is —$OR^4$, is optionally deprotected to form a compound of the formula (III) wherein Y is —OH. For example, where $R^4$ is benzyl, the deprotection can be accomplished by treating with an aqueous solution comprising 40% to 50% HBr, preferably about 48%

HBr, at a temperature of –10° to 40° C., preferably about 15° to 30° C. A preferred method of deprotection when $R^4$ is benzyl comprises treating with a palladium catalyst, such as 5% Pd/C, in the presence of formic acid.

A compound of the formula (III), wherein R is $C_6H_5CH_2$ or $CH_3$, is optionally treated with HBr to form a compound of the formula (IIIa).

In a more preferred embodiment, the present invention provides a process as described in Reaction Scheme 2 wherein the hydrazine of formula $R^1R^2CH$—NH—NH—Z (IX) is prepared by a process as shown in Reaction Scheme 3.

Reaction Scheme 3

Step A

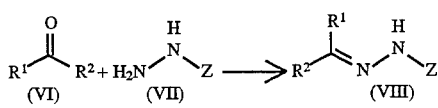

-continued
Reaction Scheme 3

Step B

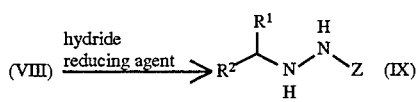

In Step A of Reaction Scheme 3, a ketone of the formula (VI), wherein $R^1$ and $R^2$ are as defined above provided that Y is —$OR^4$, is reacted with a hydrazine of the formula (VII), wherein Z is as defined above, at a temperature of 0° to 80° C., preferably at 20° to 60° C., and most preferably at about 30° to 50° C., to form a compound of the formula (VIII).

In Step B, the compound (VIII) from step A is reduced by treating with a hydride reducing agent, preferably NaBH$_4$, in a suitable solvent, such as an C$_1$–C$_4$ alcohol, preferably MeOH, EtOH or i-PrOH, to form the hydrazine (IX).

Compounds of the formula (III) wherein R$^1$ or R$^2$ is Y-substituted alkyl may contain one or more chiral centers. For such compounds, all stereoisomers, including individual stereoisomers, and mixtures or racemates thereof, are within the scope of the present invention. Such compounds are readily prepared using a starting ketone (VI) having the appropriate stereochemistry.

Compounds of the formula (IV), (VI) and (VII) are known or can be readily prepared via established methods.

R is a group of the formula

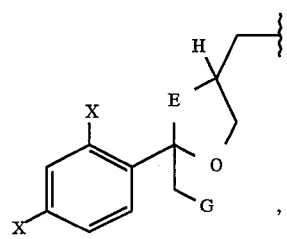

and D, E, X and G are as deemed above, can be prepared by the process described in Reaction Scheme 4.

Reaction Scheme 4

Step A

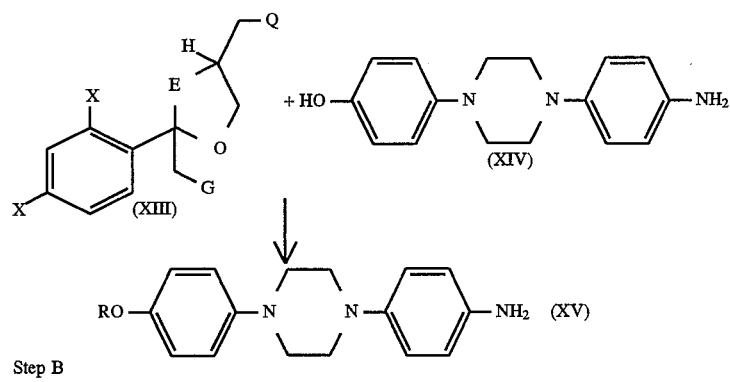

Step B

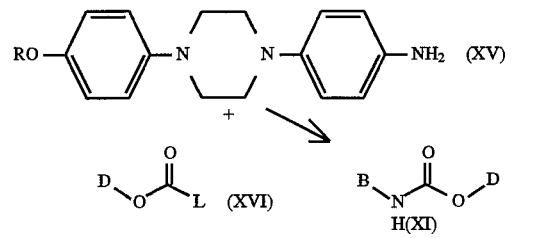

Compounds of the formula (XI)

(XI)

wherein B is a group of the formula

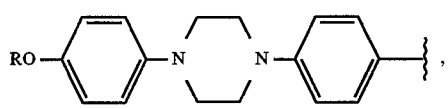

In Step A of Reaction Scheme 4, a compound of the formula (XIII), wherein Q is a leaving group, is reacted with the amino alcohol (XIV) in the presence of a base to form a compound of the formula (XV), wherein R is as defined above. The reaction occurs regioselectively via selective reaction of the phenolic hydroxyl group of compound (XIV), and does not require protection of the amino terminus of the molecule.

In Step B, the product (XV) of Step A is treated with a compound of the formula (XVI), wherein L is a leaving group and D is as defined above, to form a compound of the formula (XI) as defined above.

The present invention also comprises a process for regioselectively reacting compound (XW) with a compound of the formula (XIII) to form a compound of the formula (XV), as described in Step A of Reaction Scheme 4.

The following preparations and examples are illustrative of the process of the present invention.

PREPARATION 1

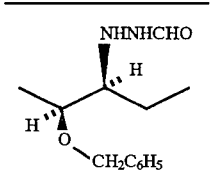

Step A:

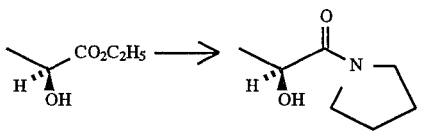

The chiral benzyloxyamide is prepared from ethyl (S)-lactate via substantially the same procedure as described in Kobayashi, et al., *Bull. Chem Soc. Jpn.*, 62, 3038–3040 (1989).

Step B:

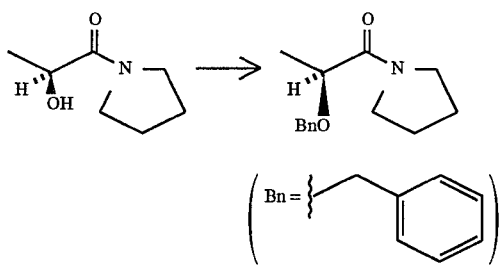

The product of Step A is converted to the corresponding benzyl ether via procedures such as the one described in Kobayashi, et al., supra. Alternatively, benzylation can be carried out via other methods known in the art such as those described in Greene, et al., "Protective Groups in Organic Synthesis", 2nd edition, p. 47–49, John Wiley & Sons, New York, (1991).

Step C:

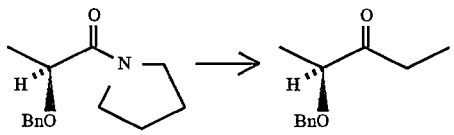

Combine 16 L of anhydrous THF and 12.5 kg of the 2-(S)-benzyloxyamide from Step A under nitrogen atmosphere and stir while cooling to –10° to –5° C. Slowly (over a period of 60 to 90 min.) add 58.4 kg of ethyl magnesium bromide as a 1M solution in THF such that the temperature remains at –10° to –3° C. Stir the reaction mixture at –4° to –2° C for 3 to 5 hours. Slowly add the reaction mixture to a stirred mixture of 125 L of TBME and 7 L of acetic acid at –10° to –5° C. such that the temperature remains at 0° to 15° C. Stir the mixture for another 20 to 30 min., then add a combination of 12.5 L of TBME, 1.25 L of HOAc and 50 mL of water. Agitate the mixture, then allow it to settle and separate the organic and aqueous layers. Wash the organic layer successively with 50 L of water, 50 L of 5% NaHCO$_3$ (aqueous), and 50 L of water. Concentrate the organic layer to a volume of 25 L via distillation at 55° to 60° C., add 25 L of TBME and cool to <30° C. Concentrate again to a volume of 25 L then concentrate in vacuo (at a temperature of about 50° C.) to give the ketone product as a residue.

Dissolve the product in 15 L of DME to give a solution of the product for use in Step D.

Step D:

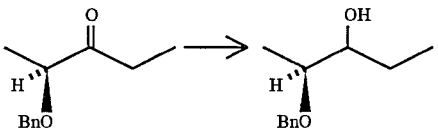

Combine 103 L of DME and 12 kg of ZnBr$_2$ and heat the mixture to 60° to 65° C. to dissolve the solids. Cool the mixture to 25° to 30° C. Slowly add this solution to a mixture of 1.24 kg of LiBH$_4$ and 21 L of DME at 0° to 10° C. such that the temperature remains at 0° to 15° C. Cool the resulting mixture to –5° to 5° C. and stir for 40 to 50 min. Slowly add the product solution from Step C such that the temperature remains at –5° to 5° C. Stir the mixture until the reaction is complete by HPLC. [HPLC analysis procedure: Dilute a 0.5 mL aliquot of the reaction mixture to a volume of 250 mL with the mobile phase MeOH/water/H$_3$PO$_4$ (50:50:0.1) and analyze 5 µL of that solution using a Zorbax® RX-ODS column and a U.V. detector.] Slowly add 15 L of acetone such that the temperature remains at 0° to 20° C. Slowly add the resulting mixture to a stirred mixture of 21 L of water and 21 kg of ice such that the temperature remains at 5° to 15° C. Slowly add a mixture of 10 L of conc. HCl, 83 L of water and 21 kg of ice, keeping the temperature at 5° to 15° C., then stir for 20 min. Add 103 L of TBME and stir for 20 min. Allow the mixture to settle and separate the aqueous and organic layers. Extract the aqueous layer with 44 L of TBME and combine the organic layers. Wash with water (4× 41 L), then concentrate the organic solution via distillation at a temperature of <55° C to a volume of 12.5 L. Add 21 L of TBME and again concentrate to a volume of 12.5 L. Concentrate in vacuo at a temperature of <50° C. to give the 2-(S)-3(R,S)-alcohol product as a residue.

Step E:

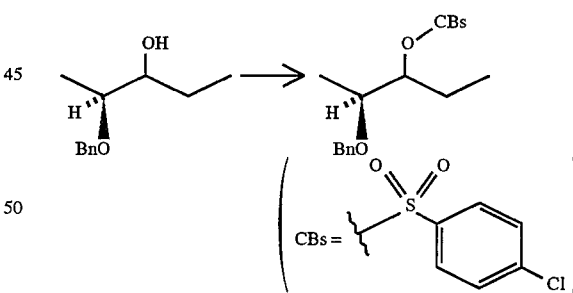

Combine 6.3 kg of the 2(S)-3(R,S)-alcohol product of Step D and 18.9 L of CH$_2$Cl$_2$ and stir while cooling to 0° to 5° C. Add 7.6 kg of p-chlorobenzenesulphonyl chloride. Slowly add a solution of 5.2 kg of DMAP in 18.9 L of CH$_2$Cl$_2$ while keeping the reaction temperature at <10° C. Stir the mixture at 15° to 25° C. until the reaction is complete by HPLC (about 16 hours). [HPLC analysis procedure: Extract a 1 mL aliquot of the mixture with dilute HCl (aqueous), then dilute to a volume of 250 mL with MeOH and analyze a 5 µL sample of that solution using a Zorbax® RxC8 column, and MeOH/water (75:25) as the mobile phase.] Add 6.3L of 25% NaOH (aqueous) and 6.3 L of water to the mixture and stir at 15° to 25° C. for about 1 hour.

Slowly add the resulting mixture to a mixture of 25.2 L of water, 31.5 kg of ice, and 2.5 L of H₂SO₄. Separate the layers and wash the organic layer successively with 63 L of 5% NaHCO₃ (aqueous), and water (2×12.6 L). Concentrate the organic layer first by distillation at 60° C., then in vacuo at <60° C. to give the chlorobenzenesulfonate of the 2-(S)-3(R,S)-alcohol as a residue.

Step F:

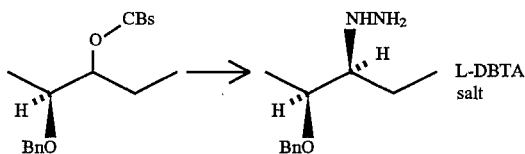

Combine 11.0 kg of the product of Step E and 16.5 L of EtOH, then add 11.0 L of hydrazine monohydrate and stir the mixture at 65° C. until the reaction is complete (about 16 hours). Cool to 15° to 25° C., add 11.0 L of water and 55.0 L of TBME, then stir for 15 min. Allow the mixture to settle, separate the layers and extract the aqueous layer with 55 L of TBME. Combine the organic layers and wash with water (2×11.0 L). Slowly add the organic solution to a solution of 11.0 kg of L-DBTA in 110.0 L of TBME and stir at 15° to 25 ° C. for 2 hours. Filter to collect the resulting precipitate and wash the solid with 22.0 L of TBME. Dry the solid in a vacuum oven at 25° C.±5° C. to give the 2(S)-3(S)-chiral hydrazine product as its L-DBTA salt.

Step G:

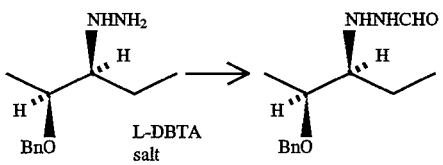

Combine 10 kg of the product of Step F, (alternatively, the product of Preparation 2 can be used), and 100 L of ethyl formate and heat the mixture at reflux for I to 2 hours until all of the solid is dissolved and the reaction is complete by HPLC. [HPLC analysis procedure: Combine 2 drops of the reaction mixture and 3 mL of 1% Et₃N in MeOH and analyze using a Zorbax® Rx-C8 column, and MeOH/water (75:25) as the mobile phase.]Add 60.0 L of TBME, then add the resulting mixture to a mixture of 2.8 kg of Na₂CO₃ and 50 L of water and stir the mixture for 15 min. Allow the layers to settle, separate the layers, then wash the organic layer successively with a solution of 0.5 kg NaHCO₃ in 10 L of water, and a solution of 0.5 kg of NaCl in 10 L of water. Concentrate the organic solution in vacuo at a temperature of <40° C., add 60.0 L of CH₂Cl₂ and distill at atmospheric pressure at about 44° C. to give the title compound as a residue.

PREPARATION 2

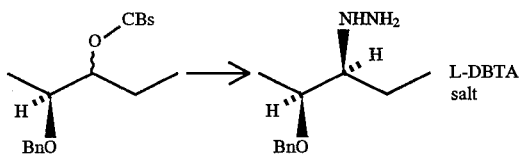

The 2(S)-3(R,S)-chlorobenzenesulfonate from Step E of Preparation I is converted to a mixture of the 2(S)-3(R)-and 2(S)-3(S)-hydrazines as their D-DBTA salts using D-DBTA and substantially the same procedure as described in Step F of Preparation 1. Using L-DBTA as described in Preparation 1, the ratio of SS:SR isomers is 91:9, while a ratio of 96:4 is obtained using D-DBTA. Recrystallization of the D-DBTA salt from a suitable solvent, such as iPrOH or a mixture of TBME and EtOH, provides the 2(S)-3(S)-hydrazine having a ratio of SS:SR of >99: 1. This D-DBTA hydrazine can be used in Step G of Preparation 1.

PREPARATION 3

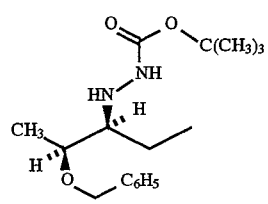

Step A:

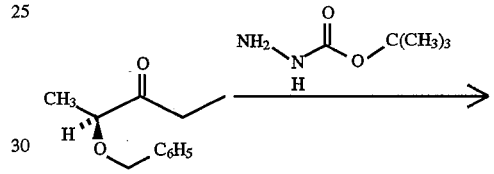

Combine 65 g (0.328 moles) of the ketone product from Step C of Preparation 1,180 mL of toluene and catalytic amount (500 mg, 2 mmoles) of PPTS, then slowly add (over a period of 15 min.) a solution of 49.15 g (0.37 moles) of t-BOC-hydrazine in 200 mL of toluene at 20°–25° C. Stir the mixture at 2-°–25° C. for about 4 hours, then filter to isolate the resulting solid. Wash the solid with cold heptane (3 X 50 mL) and dry at 50° C. in vacuo to give 80.5 g (80% yield) of the t-BOC-hydrazone product. m.p.=115.5° C.

Step B:

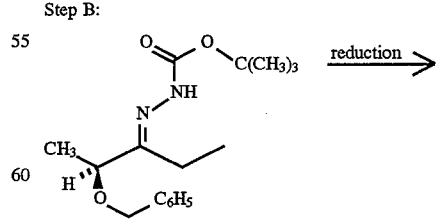

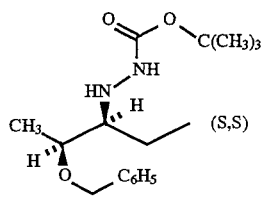

(S,S)

+

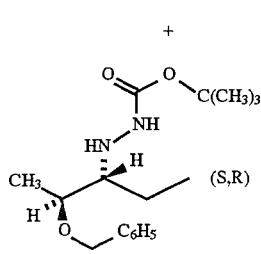

(S,R)

Dissolve 12 g (40 mmol) of the t-BOC-hydrazone product of Step A in 150 mL of $CH_2C_{12}$ and cool the mixture to $-85°$ C. Slowly add (over a period of 90 min.) 156 mL of a 1M solution of DIBAL-H in a $CH_2Cl_2$ and stir at $-80°$ to $-85°$ C. for 5 hours. Warm the mixture to $0°-5°$ C. and add 250 mL of water. Separate the phases and wash the organic phase with water (3×50 mL). Concentrate/n vacuo to give 10.6 g (86% yield) of a mixture of 94% (S,S)- and 6% (S,R)-BOC-hydrazines.

Using the hydride reducing agent, solvent and reaction conditions indicated, and following substantially the same procedure, the following results were obtained:

| Hydride Reducing Agent | Solvent | Reaction Temp. | Reaction Time (hours) | % (S,S) isomer* | % Yield |
|---|---|---|---|---|---|
| $NaBH_4$ | EtOH | 0°–5° C. | 24 | 30.9% | — |
| $NaBH_4$ | ETOH/AcOH | 0°–5° C. | 18 | — | — |
| $NaCNBH_3$ | EtOH | 0°–5° C. | 70 | 21% | — |
| $LiBH_4$ | DME | 0°–5° C. | 5 days | 41% | 86% |
| $LiBH_4$ + $ZnBr_2$ | DME | 0°–5° C. | 24 | 21 | — |
| $t-BuNH_2.BH_3$ + $TiCl_4$ | $CH_2Cl_2$ | 0°–5° C. | — | — | ** |
| $t-BuNH_2.BH_3$ + $SnCl_4$ | $CH_2Cl_2$ | –75° C. | 3 | — | ** |
| $t-BuNH_2.BH_3$ + $AlCl_3$ | $CH_2Cl_2$ | –75° C. | — | 29.4% | 45% |
| $t-BuNH_2.BH_3$ | $CH_2Cl_2$ | 0°–5° C. | 36 | 5% | — |
| $Bu_4NBH_4$ | $CH_2Cl_2$ | 0°–5° C. | 26 | — | — |
| $Bu_4NBH_4$ + $TiCl_4$ | $CH_2Cl_2$ | 0°–5° C. | — | — | ** |
| DMAB | $CH_2Cl_2$ | 0°–5° C. | 17 | — | — |
| $LiAlH_4$ | THF | 0°–5° C. | 20 | 19.2% | 67% |
| L-Selectride | THF | –60° C. | 16 | — | — |
| DIBAL-H | $CH_2Cl_2$ | –70° C. | 4 | 92.1% | 76% |
| Vitride | toluene | 0°–5° C. | 19 | 37.5% | 84% |
| DIBAL-H | $CH_2Cl_2$ | –85° C. | 6 | 91% | 69% |
| Vitride | $CH_2Cl_2$ | –85° C. | 23 | 70% | — |
| DIBAL-H | $CH_2Cl_2$ | –85° C. | 23 | 81.5% | 27% |
| DIBAL-H | THF | –80° C. | 2.5 | — | — |
| Vitride | $CH_2Cl_2$ | –85° C. | 47 | 30.7% | 45% |
| DIBAL-H | $CH_2Cl_2$ | –85° C. | 5 | 93.6% | 86% |
| DIBAL-H | toluene | –95° C. | 29 | 0% | 94% |
| DIBAL-H | toluene/$CH_2Cl_2$ | –110° C. | 18 | 0% | 96% |
| DIBAL-H | $CH_2Cl_2$ | 0°–5° C. | 0.5 | 71.4% | 68% |
| DIBAL-H | $CH_2Cl_2$/toluene (9:1) | –100° C. | 21 | 65% | 56% |
| $LiAl(OtBu)_3H$ | $CH_2Cl_2$ | –85° C. | 0.5 | 0% | — |
| DIBAL-H | $CH_2Cl_2$/$CH_3CCl_3$ | –100° C. | 72 | 65% | — |
| DIBAL-H | $CH_2Cl_2$/$CH_3CCl_3$ | –95° C. | 6 | 90% | 81% |
| DIBAL-H | $CH_2Cl_2$ | –85° C. | 5 | 93% | 70% |

*The percentage of (S,S)-BOC-hydrazine is determined by HPLC. The (S,R)-isomer comprises the remainder of the product isolated, (i.e., 0% (S,S) means that 100% (S,R) was formed).
**Decomposition occurred.

EXAMPLE 1

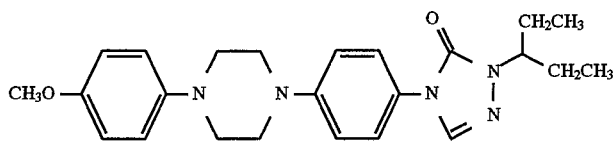

Step A:

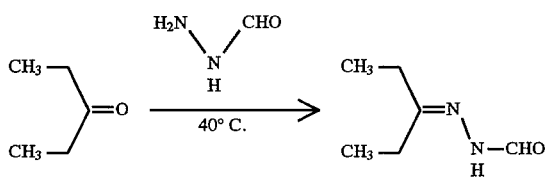

Combine 220 g (3.66 mole) of formylhydrazine and 947 g (10.99 mole) of 3-pentanone and heat the mixture at 40° C. for about 2 hours, at which time all of the hydrazine has reacted (as determined by 1H NMR). Distill at 50° C., 150 mbar, to remove the excess 3-pentanone (520 mL) leaving a residue. Add 2.7 L of n-heptane to the residue and heat the mixture to 80° C. Filter the hot mixture and concentrate the filtrate by distillation at 91°–93° C. to remove a total of 1200 mL of n-heptane. Cool the remaining mixture to 0° to 5° C. and allow the product to crystallize. Collect the solid product by filtration, wash the solid with n-heptane and dry the solid at 40° C. in vacuo to give 408.6 g (87% yield) of the formylhydrazone product.

Step B:

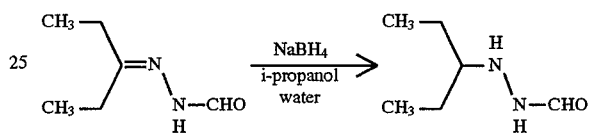

Slowly add a solution of 64.1 g (0.5 mole) of the Product of Step A in 640 mL of i-PrOH to a mixture of 20.8 g (0.55 mole) of NaBH$_4$ in 225 mL of 1:1 i-PrOH/water at 10°–15° C., over a period of 50 min. Stir the resulting mixture at 10°–15° C. for about 90 min., then add 125 mL of acetone and stir for 1 hour at 10°–20° C. Distill at 50° C., 200 mbar, to remove the solvent and treat the resulting residue with 300 mL of water and 200 mL of TBME. Separate the phases and extract the aqueous phase with 50 mL of TBME. Combine the organic phase and extract and wash successively with 100 mL of water and 2×50 mL of brine, then dry over Na$_2$SO$_4$. Distill off the solvent at 50° C., 150 mbar, then add toluene and azeotropically distill residual water to give 57 g (87.7% yield) of a residue. Distill the residue (50° C.)to give a 55% yield of the formyl hydrazine product. m.p.=35°–37° C.

Step C:

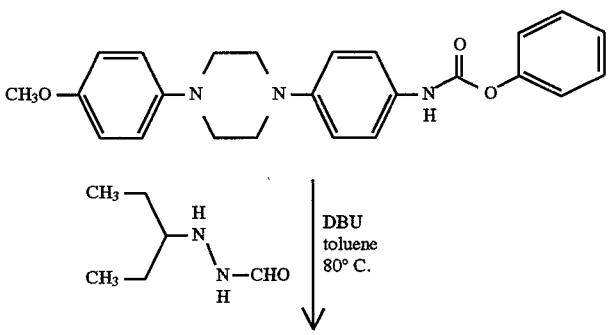

-continued

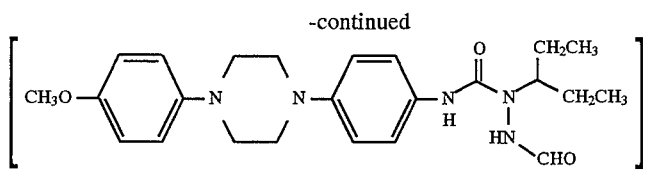

|toluene
|reflux
↓

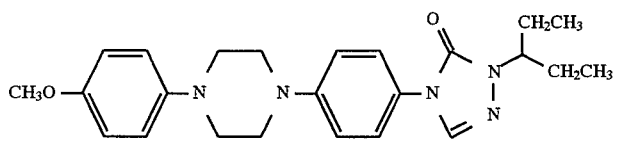

Combine 1.43 g (11 mmol) of the Product of Step B, 4.03 g (10 mmol) of the methoxy carbamate, 15.3 mg (0.1 mmol) of DBU and 50 mL of toluene and heat to 80° C. for about 7.5 hours to give a mixture containing the uncyclized intermediate, which can be isolated if desired. Heat the mixture at reflux for about 8 hours to complete the formation of the triazolone. Distill off the toluene to give a residue and treat the residue with 15 mL of MeOH. Cool the mixture to 0°–5° C. and stir for 1 hour. Filter to collect the solid product, wash the solid with 2×10 mL of MeOH, then dry the solid at 50° C. in vacuo to give the desired triazolone product (84% yield).

Step B:

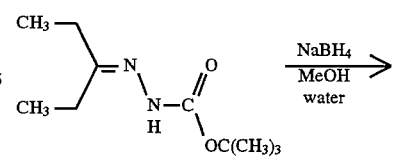

EXAMPLE 2

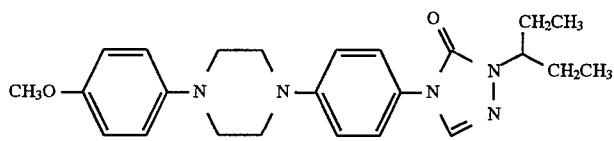

Step A:

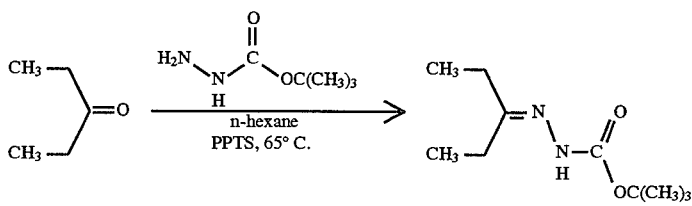

Combine 132 g (1.0 mole) of BOC-hydrazine, 0.2 g (0.8 mmol) of PPTS and 400 mL of n-hexane and heat the mixture to 40° C. Add 107.6 g (1.25 mole) of 3-pentanone and heat the mixture to 60° C. for 15 min., then stir at 50° C. for 1–2 hours. Cool the mixture to 15° C. and filter to collect the solid product. Wash the solid with 150 mL of n-hexane and dry the solid at 50° C. in a draft oven to give 184 g (91% yield) of the BOC-hydrazone product. m.p.= 109°–110° C.

-continued

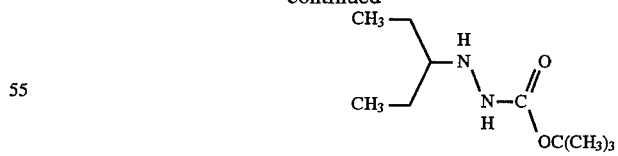

Combine 125 g (0.625 mole) of the hydrazone product of Step A, 875 mL of MeOH and 375 mL of water and add a few drops of 30% NaOH (aqueous) to adjust to pH=11. Add 47.5 g (1.26 mole) of NaBH₄ to the mixture at 20°–25° C. and stir for 16 hours. Add a few drops of concentrated HCl to readjust to pH=11.5, then add 15.0 g (0.397 mole) of NaBH₄ and stir for 15 hours at 20°–25° C. Add conc. HCl to readjust to pH=11.5, then add 10 g (0.26 mole) of NaBH₄ and stir for 2 hours at 20°–25° C. Add 500 mL of TBME, filter to remove the resulting precipitate and wash the solid with 500 mL of TBME. Add 500 mL of water to the filtrate and separate the phases. Extract the aqueous phase with 2×500 mL of TBME. Combine the organic phases and wash with 500 mL of water, then with 500 mL of brine. Distill off the solvent from the organic phase at 50° C., 200 mbar, to give a residue. Treat the residue with 300 mL of TBME, filter and concentrate the filtrate in vacuo to give a 93% field of the BOC-hydrazine derivative product.

the mixture at 48°–52° C. for about 70 min. Cool the mixture to 20° C. and 22 mL of 30% NaOH (aqueous) to adjust to pH=12.5. Cool the mixture to 10° C. and stir for 1 hour. Filter and wash the solids with 30 mL of water, then dry the solids in vacuo to give an 88% yield of the product.

Step C:

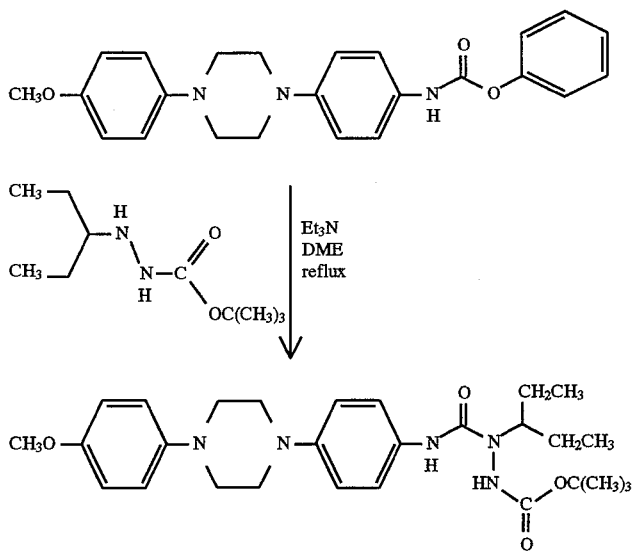

Combine 12.6 g (62.4 mmol) of the BOC-hydrazine derivative of Step B, 20.1 g (49.8 mmol) of the carbamate, 5.5 g (54.35 mmol) of Et₃N and 400 mL of DME and heat the mixture to reflux (about 85° C.) for about 16 hours. Filter the mixture and cool the filtrate to 0°–5° C. and stir at 0°–5° C. for 1 hour. Collect the resulting solid by filtration, wash the solid with 80 mL of DME and dry the solid at 50° C. in a draft oven to give an 82% yield of the uncyclized product.

Step D:

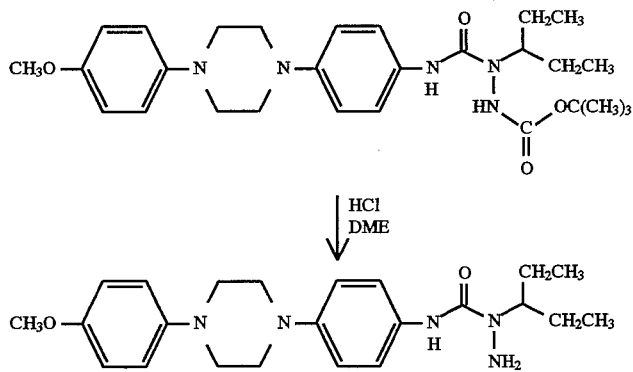

Combine 10.2 g (19.96 mmol) of the product of Step C, 100 mL of DME and 36 mL of concentrated HCl and heat Step E:

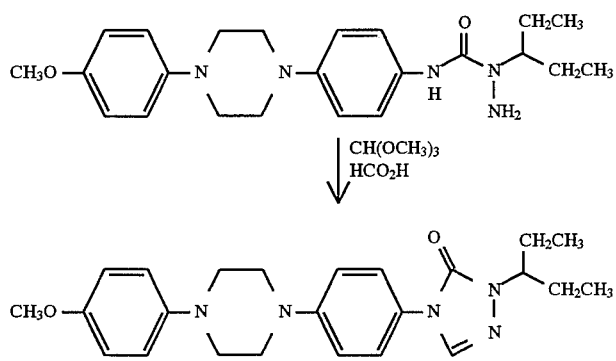

Combine 4 g (9.73 mmol) of the product of Step D and 36 mL (328.7 mmol) of trimethyl orthoformate and heat the mixture to 75° C. Add 3 g (65 mmol) of formic acid, then heat to 100° C. for 30 min. Cool the mixture to 10° C. and stir for 1 hour. Filter to collect the solids, wash the solids with 10 mL of $CH_3CN$ and n-hexane, then dry the solids in vacuo to give 3.4 g (82% yield) of the triazolone product.

EXAMPLE 3

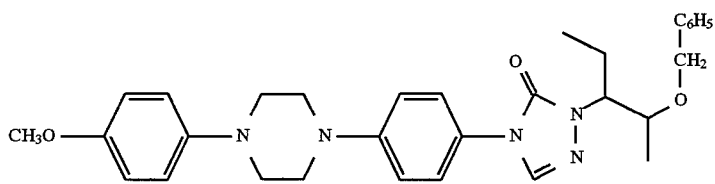

Step A:

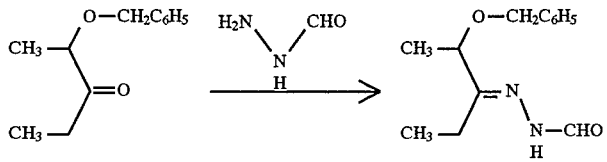

Formylhydrazine and 2-benzyloxy-3-pentanone are reacted using substantially the same conditions as described in Example 1, Step A, to form the formylhydrazone product.

Step B:

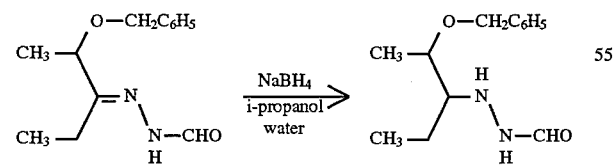

The formylhydrazone of Step B is reduced using $NaBH_4$ following substantially the same procedure as described in Example 1, Step B, to form the formylhydrazine derivative product.

Step C:
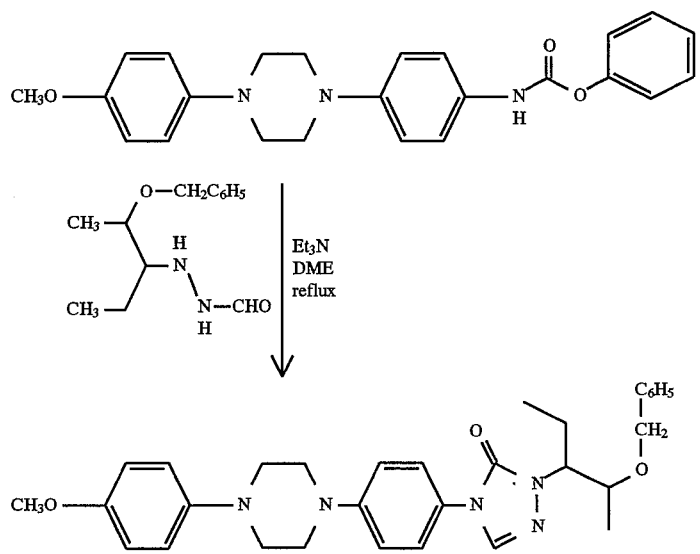
The N-(benzyloxyalkyl)triazolone product is prepared from the product of Step B and the carbamate, using Et₃N as the base and DME as solvent, via substantially the same procedure as described in Example 1, Step C.
EXAMPLE 4
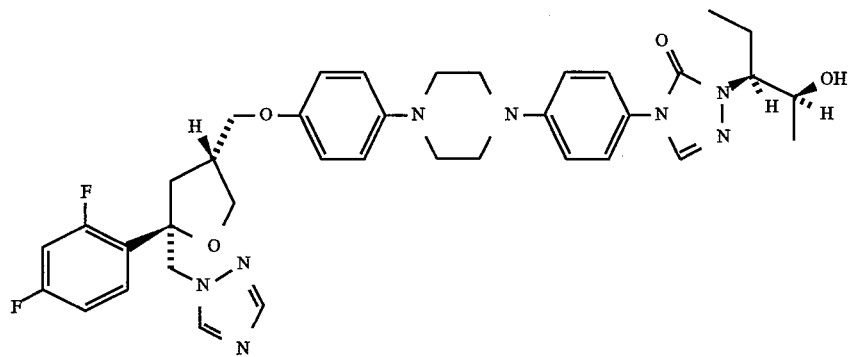
Step A:
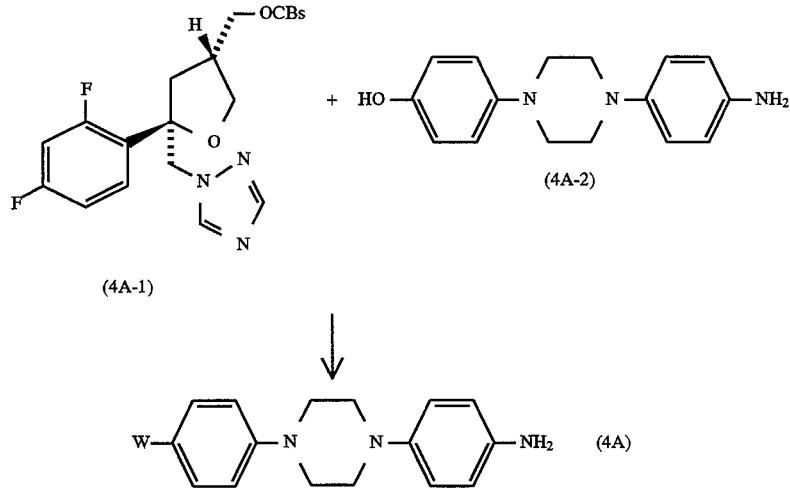

-continued wherein W = 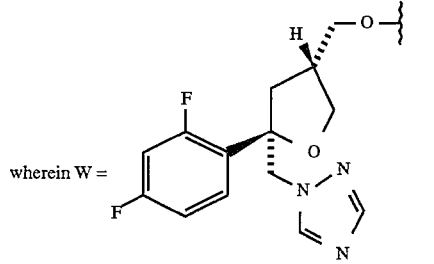

Add 50 g of the amino alcohol (4A-2) to a stirred solution of 750 mL DMSO at room temperature and 12 g NaOH dissolved in 84 mL H₂O. Stir the resulting mixture for 5 min and then add 100 g of the chiral chlorobenzenesulfonate (4A-1). Stir overnight at room temperature and then dilute with 3 L of water. Cool to about 5° C., stir for 0.5 hr and filter. Wash the solid thus obtained with hexane to give 97.5 g of the product (4A). MS: FAB, 547 (M+H)

Step B:

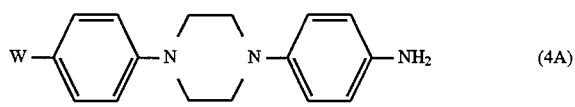

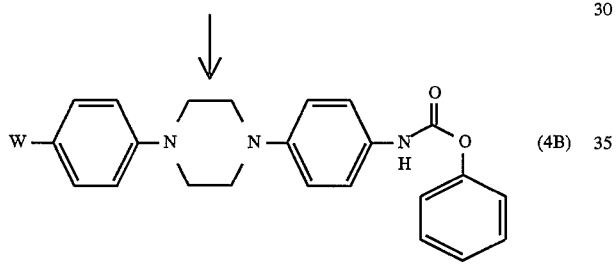

Slowly add 21.5 mL of PhOCOCl to a stirred solution of 85 g of the product (4A) of Step A, wherein W is as defined for Step A, in 650 mL of CH₂Cl₂ at room temperature. Stir at room temperature until the reaction is complete (2 to 8 hr). Cool the mixture to 0° C., wash with saturated NaHCO₃ (aqueous) such that the pH of the aqueous layer remains basic. Separate the layers and extract the aqueous layer with CH₂Cl₂. Combine the CH₂Cl₂ layers, then add 1.5 L of H₂O and 2.5 L of hexane. Cool to 0° C. and filter to collect the resulting solid. Wash the solid sequentially with water, 50% MeOH/H₂O, and then hexane. Dry the solid to give 100.5 g of the product (4B), wherein W is as defined above. MS: FAB, 667 (M+H)

Step C:

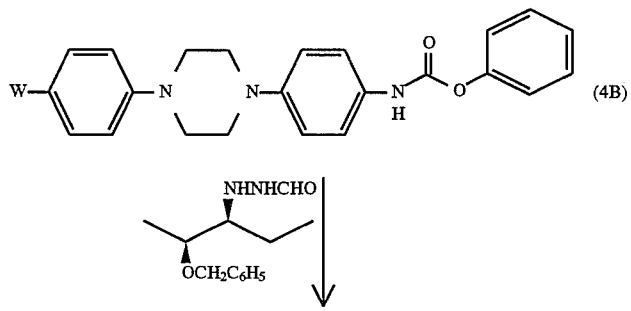

Step C:

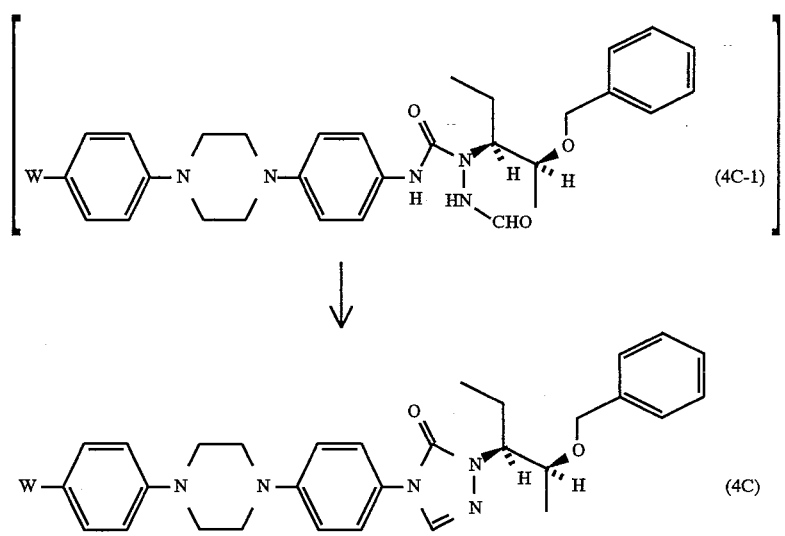

Combine 347 g of the product (4B) of step B, 137 g of the chiral hydrazine of Preparation 1, 85 g of type 4Å molecular sieves, 0.8 g of DBU and 1400 mL of toluene, and heat the mixture at 75° to 85° C. for 12–24 hrs to form the intermediate (4C-1). Raise the temperature to 100° to 110° C. and continue heating for 24 to 48 hrs. Cool the mixture to 70° C. and filter through Celite®, washing with 700 mL of hot toluene. Distill the filtrate under vacuum to a volume of 1000 mL, then cool to 40° C. and add 2400 mL of $CH_2Cl_2$. Wash the resulting solution sequentially with 0.5M aqueous NaOH (2×800 mL), 200 mL of water, 235 mL of 1M HCl (aqueous), 200 mL of water, and 250 mL of 5% $NaHCO_3$ (aqueous). Add 34 g of Darco® the solution, stir for 10 to 15 min, then filter through Celite®, washing with 400 mL of $CH_2Cl_2$. Distill the filtrate at atmospheric pressure to a volume of 1000 mL, then distill in vacuo (temperature <70° C.) to give the product (4C).

350 mL of $HCO_2H$. Rinse with an additional 350 mL of $HCO_2H$ to ensure complete transfer of material. Stir the mixture at 20 ° C. overnight, then at 40° C. for 24 hrs. Filter the resulting mixture through Celite®, washing with 350 mL of $HCO_2H$, and then with 700 mL of MeOH. Concentrate the filtrate/n vacuo to a residue. Add 3500 mL of MeOH and 694 mL of $NH_4OH$ (aqueous) to the residue and heat the mixture at reflux for 1 to 2 hrs. Cool the mixture to 15° to 25° C. and filter to collect the resulting solid. Wash the solid with 1400 mL of 1:1 MeOH/water, then air dry the solid in a draft oven at 40° C. to give 300.5 g of the title compound (1).

Step D:

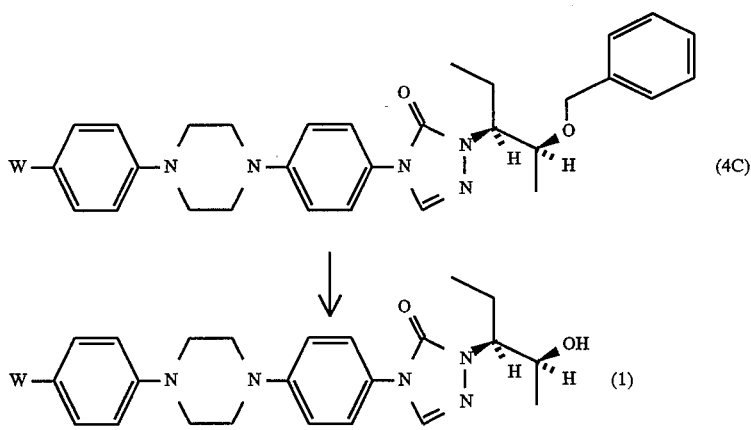

Cool the product (4C) from Step C to 50° C., add 350 mL of $HCO_2H$, continue cooling to 20° C., and add another 350 mL of $HCO_2H$ (350 mL). Add the resulting formic acid solution to a slurry of 85 g of 5% Pd/C (50% water wet) in

EXAMPLE 5

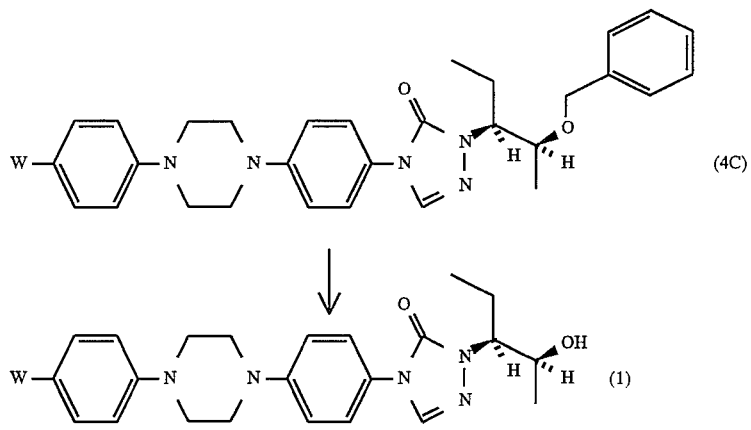

Combine 12.6 g (15.9 mmol) of the product (4C) of Example 4, Step C, and 300 mL of 48% HBr (aqueous). Stir the resulting mixture at room temperature for 24 hrs., then cool to 0° C. and add 4 N NaOH (aqueous) to adjust the pH of the mixture to 7.5–8. Stir for 30 min. at 0° C. then falter to collect the resulting solid. Wash the solid with 300 mL of water, then partition the solid between 100 mL of $CH_2Cl_2$ and 100 mL of brine. Separate the layers and extract the aqueous layer with $CH_2Cl_2$ (3×50 mL). Combine the organic layers and wash with 50 mL of water, then dry over anhydrous $MgSO_4$. Concentrate in vacuo to a solid residue and recrystallize from about 60 mL of 9:1 water/acetone. Dry the recrystallized solid in a vacuum oven for 18 hrs. at 45° C. to give 6.94 g of the title compound (1). A second crop of 1.23 g of the title compound (1) is obtained from the mother liquor of the recrystallization. These materials were combined and slurried in hot TBME/hexane (1:2), cooled to 0° C., then filtered to give 8.2 g of the title compound (1). MS m/z=701.4 (M+1)

add 5.76 mL of $C_6H_5OC(O)Cl$. Stir the reaction mixture until the reaction is complete (4 to 18 hrs.), then dilute with water, cool to 0° to 5° C., and filter to obtain 17.4 g of the hydroxy carbamate product as a solid. MS: FAB, 390 (M+H).

EXAMPLE 6

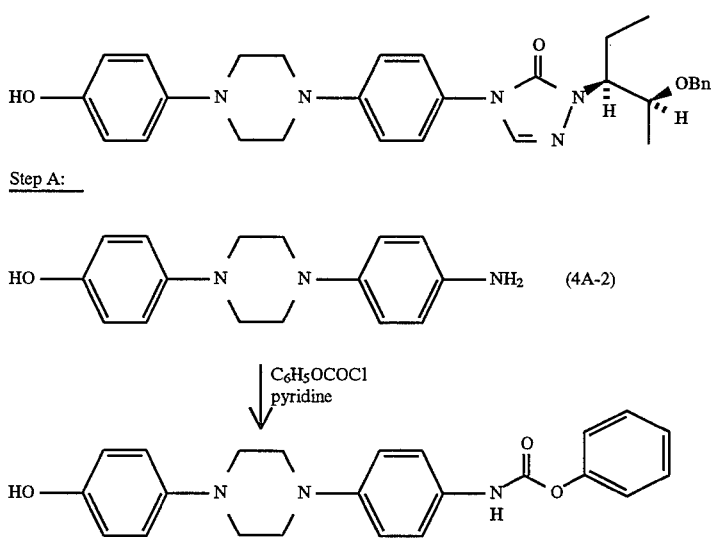

Step A:

Combine 12.0 g of the amino alcohol (4A-2), 110 mL of DMF, and 3.6 mL pyridine at room temperature, then slowly Step B:

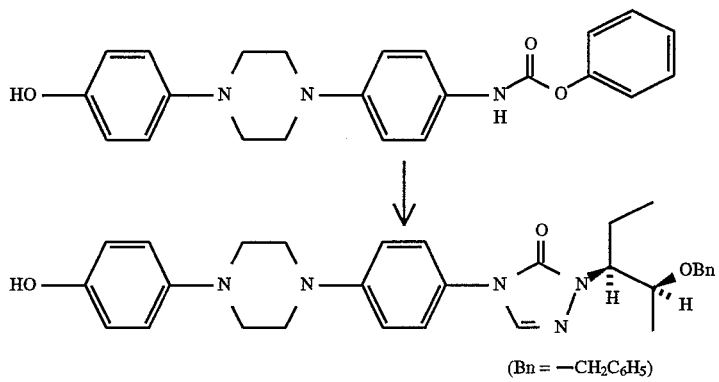

(Bn = —CH₂C₆H₅)

The product of Step A is converted to the chiral N-alkyl triazolone by heating with the chiral hydrazine of Preparation 1 under substantially the same conditions as described for Step C of Example 4.

EXAMPLE 7

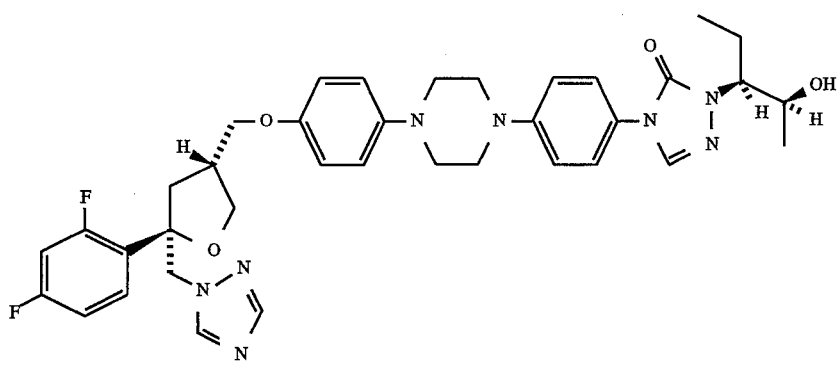

Step A:

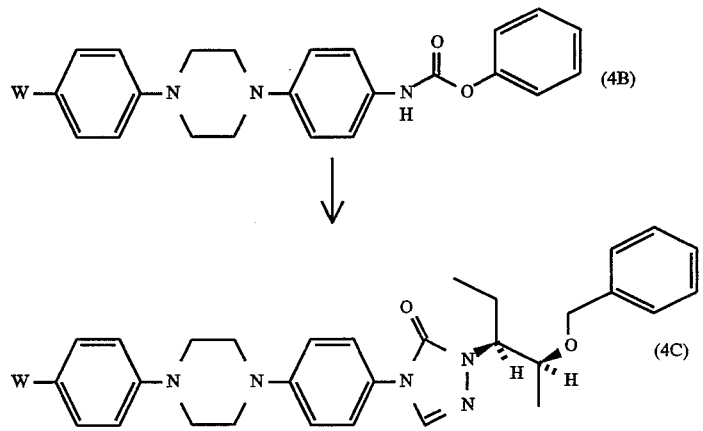

Combine 347 g Of the product (4B) of Example 4, Step B, 137 g of the product of Preparation 1, 0.8 g of DBU, 1100 mL of toluene and 85 g of molecular sieves and heat the mixture at 75° to 80° C. for three days. Cool to 70° C. and filter the hot mixture through Celite®, washing the filter cake with 700 mL of hot toluene. Combine the filtrate and washing and concentrate/n vacuo at <50° C. to a volume of 1000 mL. Cool to 40° C., add 2400 mL of CH₂Cl₂, then cool to 20° C. Wash (2×800 mL) with a solution prepared from 190 mL of 25% NaOH (aqueous) and 1400 mL of water, then wash successively with 200 mL of water, a solution of 35 mL concentrated HCl and 200 mL of water, and 250 mL of 5% NaHCO₃ (aqueous). Add 34 g of Darco® then filter through Celite®, washing the filter cake with 400 mL of CH₂Cl₂. Distill at about 50° C. to remove the CH₂Cl₂, then under vacuum at 68° C. to remove toluene, giving a residue. Cool the residue to 50° C. and add 350 mL of formic acid. Cool to 20° C. and add another 350 mL of formic acid to give a solution of the product to be used directly in Step B.

Step B:

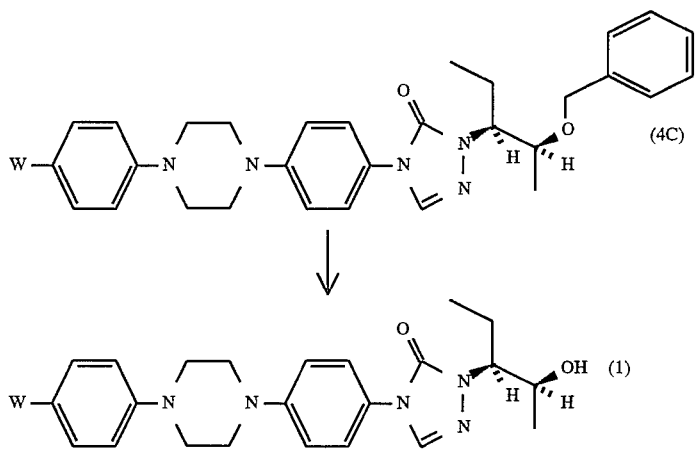

Slowly add the product solution of Step A to a mixture of 85 g of 5% Pd/C and 350 mL of formic acid at 20° C. Stir the resulting mixture at 21 ° C. for about 15 hours, then heat to 35° to 40° C. and stir for 24 hours more. Cool the mixture to 20° C. and filter through Celite®, washing the filter cake with 390 mL of formic acid, then with two 350 mL portions of MeOH. Combine the filtrate and washings and concentrate in vacuo at <70° C. to a residue. Add 1750 mL of MeOH to the residue and redistill under vacuum to a residue. Add 1000 mL of MeOH to the residue and stir overnight at room temperature. Dilute the solution with another 2470 mL of MeOH, cool to 20° C. then add 694 mL of 28% NaOH (aqueous). Heat the mixture at reflux for 24 hours then cool slowly to 41 ° C. to form a precipitate. Maintain the temperature at 40° to 45° C. for 30 min., then cool to 15° to 25° C. and stir for 2 hours. Filter to collect the precipitate and wash the precipitate with 1400 mL of 1:1 MeOH/water. Dry the solid in a draft oven at 40° C. to give 300.5 g of the title compound (1).

EXAMPLE 8

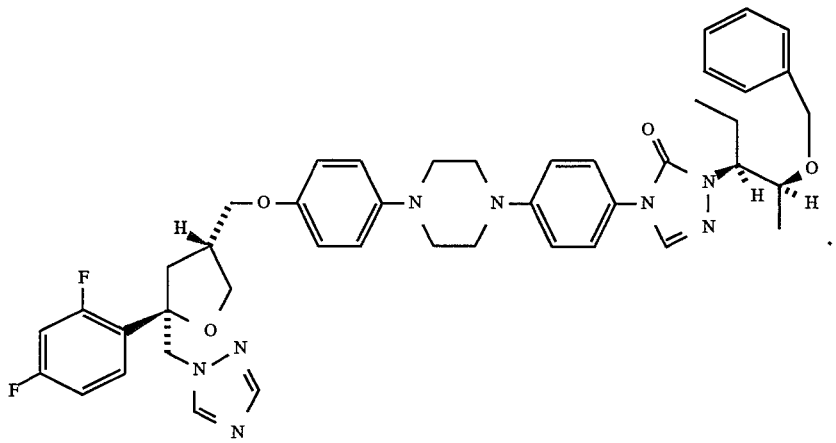

The product of Example 6 is reacted with the chiral chlorobenzenesulfonate (4A-1) of Example 4 under substantially the same conditions as described in Example 4, Step A, to give the desired compound.

EXAMPLE 9

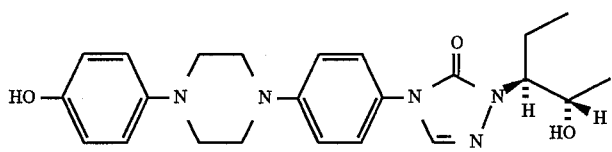

Step A:

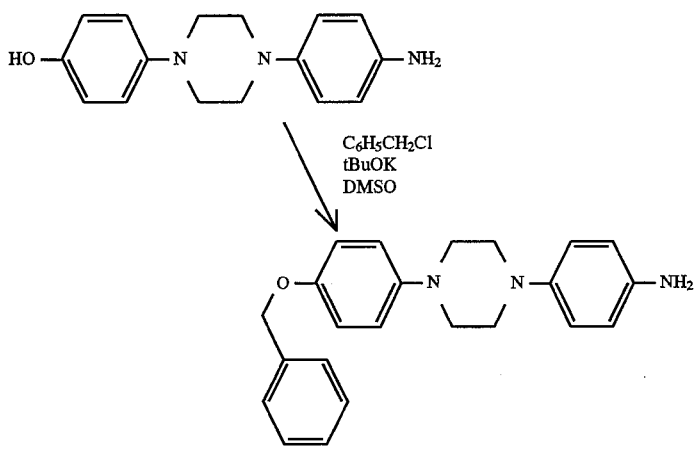

Combine 2.16 g (8.0 mmol) of the aminophenol, 32 mL of DMSO and 0.95 g (8.5 mmol) of tBuOK at 0° C. Stir the resulting mixture at room temperature for 30 min., then add 1.04 g (8.2 mmol) of benzyl chloride and stir at room temperature for 24 hours. Dilute the mixture with 150 mL of water and filter to collect the resulting solid. Wash the solid with 50 mL of 10% MeOH in water, then dry in vacuo (40 torr) at 60° C. to give 2.8 g (100% yield) of the product.

Step B:

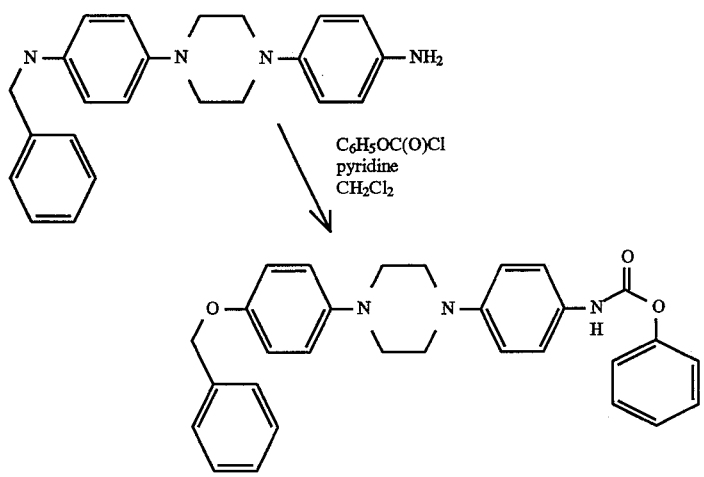

Combine 1.80 g (5.0 mmol) of the product of Step A, 30 mL of $CH_2Cl_2$, 0.55 g (7.0 mmol) of pyridine and 0.94 g (6.0 mmol) of phenyl chloroformate at room temperature and stir for 3 hours. Add o.55 g or pyridine and 0.5 g of phenyl chloroformate and stir for 1 hour. Dilute with 20 mL of water and stir for 1 hour. Filter to collect the resulting solid to give 2.0 g (83% yield) of the product. MS (M+1)=480.5.

Step C:

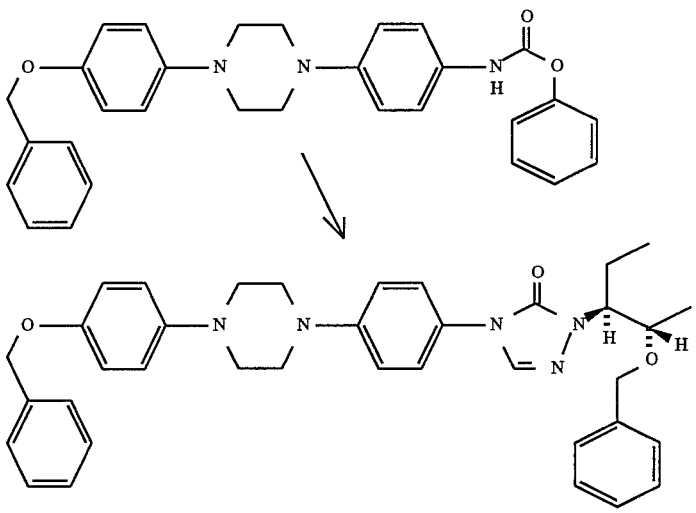

The product of Step B is reacted with the chiral hydrazine of Preparation 1 via substantially the same procedure as described for Example 4, Step C to give the chiral triazolone product.

Step D:

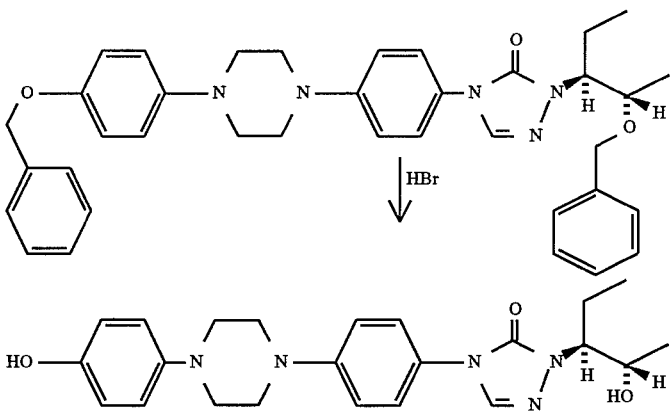

Combine 50 mg (0.86 mmol) of the Product of Step C and 3 mL of 48% HBr (aqueous) at room temperature. Stir the mixture for 24 hours, then concentrate/n vacuo to give 60 mg of the title compound as its HBr salt. MS: (M) =409.4; (M+1)=410.4; (M+2)=411.4.

We claim:

1. A process for preparing a triazolone compound of the formula

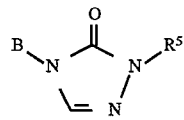

wherein:

B is aryl, substituted aryl or a group of the formula

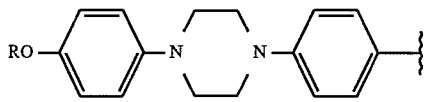

wherein

R is C$_6$H$_5$CH$_2$, CH$_3$, H or a group of the formula

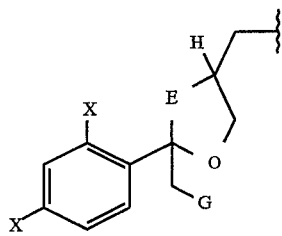

where

G is imidazolyl or triazolyl, E is CH$_2$ or O, and each X is independently F or Cl; and R$^5$ is C$_1$–C$_{20}$ alkyl or substituted C$_1$–C$_{20}$ alkyl; comprising heating a mixture of a compound of the formula

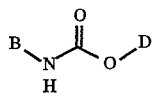

wherein:

B is as defined above, and

D is C$_1$–C$_6$ alkyl, aryl, substituted aryl or aryl(C$_1$–C$_6$ alkyl); with:
(a) a hydrazine derivative of the formula Z—NH—NH—R$^5$, wherein R$^5$ is C$_1$–C$_{20}$ alkyl or substituted C$_1$–C$_{20}$ alkyl, and Z is —CHO; or
(b) a hydrazine derivative of the formula Z—NH—NH—R$^5$, wherein R$^5$ is as defined above and Z is —C(O)OC(CH$_3$)$_3$ or —C(O)OCH$_2$C$_6$H$_5$, followed by hydrolyzing the Z group, and heating with a trialkylorthoformate and formic acid, in the optional presence of base, to form a triazolone;

wherein

"substituted alkyl" means an alkyl group bearing one to three substituents selected from the group consisting of halo, C$_1$–C$_6$ alkoxy, and aryloxy;

"aryl" means a carbocyclic aromatic group; and

"substituted aryl" means an aryl group bearing one to three substituents selected from the group consisting of halo, alkyl, and C$_1$–C$_6$ alkoxy.

2. The process of claim 1 wherein a base is present in the mixture.

3. A process for preparing a triazolone compound of the formula

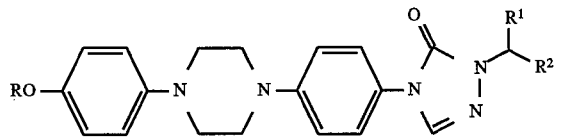

wherein:

R is C$_6$H$_5$CH$_2$, CH$_3$, H or W;

R$^1$ and R$^2$ are independently C$_1$–C$_6$ alkyl or Y-substituted C$_1$–C$_6$ alkyl, wherein Y is —OH or —OR$^4$, and wherein R$^4$ is a hydroxyl protecting group;

or R$^1$ and R$^2$ together with the carbon atom to which they are attached comprise a C$_4$–C$_7$ carbocyclic ring; and W represents

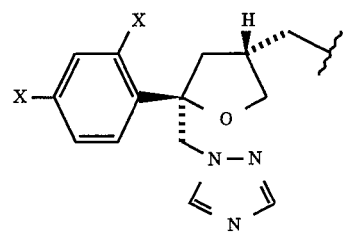

wherein each X is independently Cl or F; comprising heating a mixture of a compound of the formula

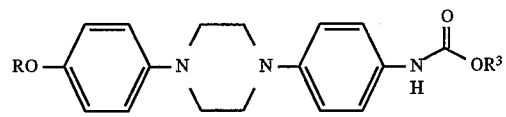

wherein R is C$_6$H$_5$CH$_2$, H, CH$_3$ or W and R$^3$ is phenyl, with:
(a) a hydrazine derivative of the formula R$^1$R$^2$CH—NH—NH—Z, wherein R$^1$ and R$^2$ are as defined above, provided that Y is —OR$^4$, and Z is —CHO; or
(b) a hydrazine derivative of the formula R$^1$R$^2$CH—NH—NH—Z, wherein R$^1$ and R$^2$ are as defined above, provided that Y is —OR$^4$, and Z is —C(O)OC(CH$_3$)$_3$ or —C(O)OCH$_2$C$_6$H$_5$, followed by hydrolyzing the Z group, and heating with a trialkylorthoformate and formic acid, in the optional presence of base, to form a triazolone of the formula

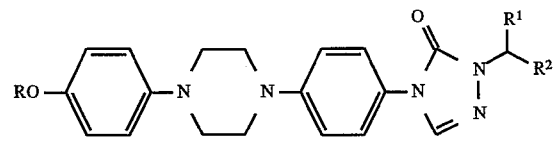

wherein R, R$^1$ and R$^2$ are as defined above provided that Y is —OR$^4$, and:
i) where Y is present, for preparing a compound where Y is —OH, deprotecting to form a triazolone of the formula

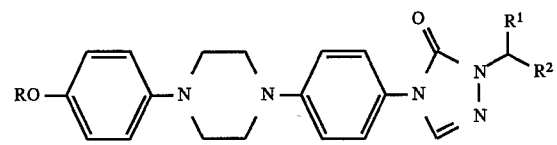

wherein R, R$^1$ and R$^2$ are as defined, and Y is —OH; or
(ii) for forming a triazolone where R is H, treating a triazolone where R is C$_6$H$_5$CH$_2$ or CH$_3$ with HBr to form a triazolone of the formula

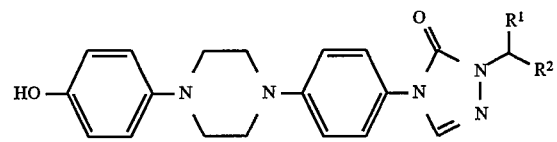

wherein R$^1$ and R$^2$ are as defined above.

4. The process of claim 3 wherein a base is present in the mixture.

5. The process of claim 4 wherein the base is selected from a tertiary amine base, hydroxide base, 1,8-diazabicyclo[5.4.0]undec-7-ene, 1,5-diazabicyclo[4.3.0]non-5-ene, 1,4-diazabicyclo [2.2.2]octane, a moderate base and phosphazene base.

6. The process of claim 5 wherein the base is triethylamine, 1,8-diazabicyclo[5.4.0]undec-7-ene, $K_2CO_3$ or phosphazene base.

7. The process of claim 3 for preparing a triazolone wherein R is W, and $R^1$ and $R^2$ are independently $C_1-C_6$ alkyl or Y-substituted $C_1-C_6$ alkyl, wherein Y is —OH or —$OR^4$, and $R^4$ is a benzyl group.

8. The process of claim 7 wherein one of $R^1$ or $R^2$ is ethyl and the other is Y-substituted ethyl.

9. The process of claim 8 wherein the triazolone has the formula

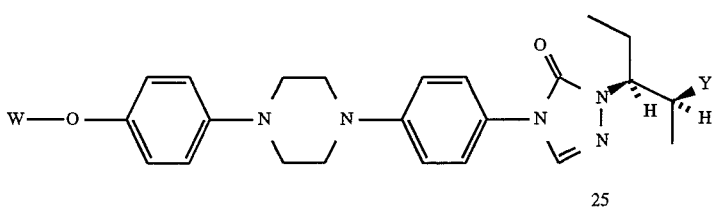

wherein;
Y is —OH or —$OR^4$, wherein $R^4$ is hydroxyl protecting group, and
W represents

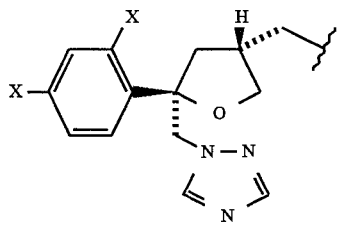

wherein each X is independently Cl or F.

10. The process of claim 9 wherein a base is present in the mixture.

11. The process of claim 10 wherein the base is selected from a tertiary amine base, hydroxide base, 1,8-diazabicyclo[5.4.0]undec-7-ene, 1,5-diazabicyclo[4.3.0]non-5-ene, 1,4-diazabicyclo[2.2.2]octane, a moderate base and phosphazene base.

12. The process of claim 11 wherein the base is triethylamine, 1,8-diazabicyclo[5.4.0]undec-7-ene, $K_2CO_3$ or phosphazene base.

13. The process of claim 7 wherein the deprotection in step (i) comprises: (a) treating with a solution of 40% to 50% HBr in water at a temperature of −10° C. to 40° C.; or (b) treating with a palladium hydrogenation catalyst and formic acid.

14. The process of claim 13 wherein the solution is about 48% HBr and the temperature is 15° C. to 30° C.

15. The process of claim 3 wherein the hydrazine derivative of the formula $R^1R^2CH$—NH—NH—Z is prepared by a process comprising the steps:

(a) reacting a ketone of the formula $R^1$—C(O)—$R^2$, wherein $R^1$ and $R^2$ are as defined in claim 3, with a hydrazine of the formula $H_2N$—NH—Z, wherein Z is as defined in claim 3, at a temperature of 0° to 80° C., to form a compound of the formula

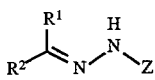

wherein $R^1$, $R^2$ and Z are as defined in claim 3; and (b) reducing the product of step (a) by treating with a hydride reducing agent in a suitable solvent.

16. The process of claim 15 wherein the hydride reducing agent is sodium borohydride and the solvent is a $C_1-C_4$ alcohol.

17. The process of claim 1 wherein B is a group of the formula

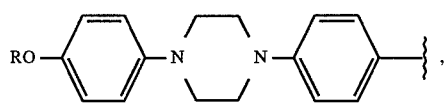

R is a group of the formula

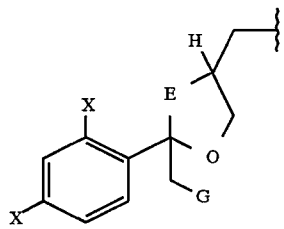

wherein X, E and G are as defined in claim 1, wherein the compound of formula

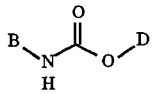

wherein B and D are as defined in claim 1, is prepared by a process comprising the steps:

(a) reacting a compound of the formula

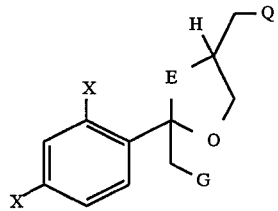

wherein Q is a leaving group and E, X and G are as defined in claim 1, in the presence of a base with the amino alcohol of the formula

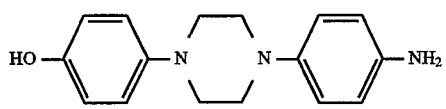

to form a compound of the formula

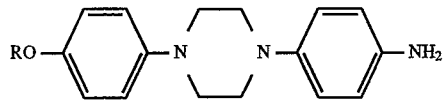

wherein R is as defined above; and (b) treating the product of step (a) with a compound of the formula

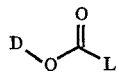

wherein L is a leaving group and D is as defined in claim 1 to form a compound of the formula

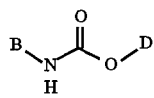

wherein B and D are as defined in claim 1.

18. The process of claim 3 wherein R is W and the compound of formula

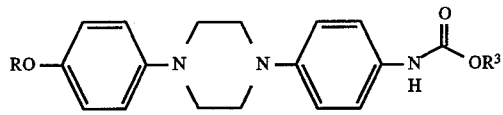

wherein R and $R^3$ are as defined in claim 3, is prepared by a process comprising the steps:

(a) reacting a compound of the formula

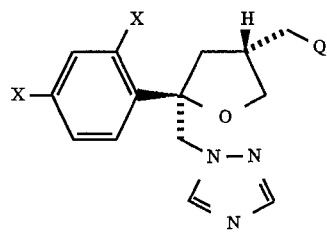

wherein Q is a leaving group and X is as defined in claim 3, in the presence of a base with the amino alcohol of formula

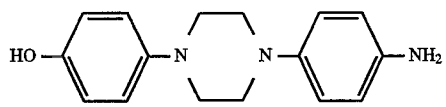

to form a compound of the formula

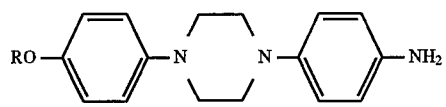

wherein R is as defined in claim 3; and (b) treating the product of step (a) with a compound of the formula

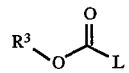

wherein L is a leaving group selected from Cl, Br or I, and $R^3$ is as defined in claim 3, to form a compound of the formula

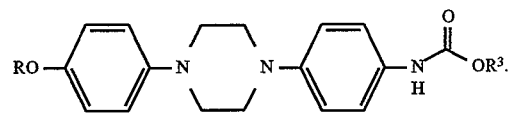

19. The process of claim 18 wherein Q is $-OS(O)_2R^5$ wherein $R^5$ is $C_1$–$C_4$ alkyl, $CF_3$, aryl, substituted aryl or aryl($C_1$–$C_4$ alkyl); wherein "aryl" means a carbocylic aromatic group; and
"substituted aryl" means an aryl group bearing one to three substituents selected from the group consisting of halo, alkyl, and $C_1$–$C_6$ alkoxy.

* * * * *